US011951288B2

(12) United States Patent
Bihlmaier

(10) Patent No.: US 11,951,288 B2
(45) Date of Patent: Apr. 9, 2024

(54) PULSATILE OR RESONATING FLUSH SYRINGE

(71) Applicant: Becton, Dickinson and Company, Franklin Lakes, NJ (US)

(72) Inventor: Bryan Bihlmaier, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 835 days.

(21) Appl. No.: 16/965,298

(22) PCT Filed: Jan. 25, 2019

(86) PCT No.: PCT/US2019/015208
§ 371 (c)(1),
(2) Date: Jul. 27, 2020

(87) PCT Pub. No.: WO2019/147977
PCT Pub. Date: Aug. 1, 2019

(65) Prior Publication Data

US 2021/0113772 A1 Apr. 22, 2021

Related U.S. Application Data

(60) Provisional application No. 62/622,907, filed on Jan. 28, 2018.

(51) Int. Cl.
*A61M 5/31* (2006.01)
*A61M 5/14* (2006.01)
*A61M 5/168* (2006.01)

(52) U.S. Cl.
CPC ............ *A61M 5/3134* (2013.01); *A61M 5/14* (2013.01); *A61M 5/16804* (2013.01); *A61M 5/16877* (2013.01); *A61M 2005/1403* (2013.01); *A61M 2206/16* (2013.01)

(58) Field of Classification Search
CPC .. A61M 2005/1403; A61M 2005/3128; A61M 2039/0018; A61M 2206/16; A61M 39/225; A61M 5/001; A61M 5/14; A61M 5/16804; A61M 5/16813; A61M 5/16877; A61M 5/16881; A61M 5/3134
See application file for complete search history.

(56) References Cited

U.S. PATENT DOCUMENTS

| | | | | |
|---|---|---|---|---|
| 6,616,677 | B2 * | 9/2003 | Gordon | A61M 5/30 604/294 |
| 7,976,529 | B2 | 7/2011 | Carpenter | |
| 8,491,537 | B2 | 7/2013 | Kosinski et al. | |
| 2002/0007143 | A1 | 1/2002 | Gordon | |
| 2002/0116021 | A1 | 8/2002 | Gordon | |
| 2010/0076370 | A1 | 3/2010 | Howlett et al. | |
| 2011/0009829 | A1 | 1/2011 | Kosinski et al. | |

(Continued)

FOREIGN PATENT DOCUMENTS

EP 0627231 A2 12/1994

*Primary Examiner* — Shefali D Patel
(74) *Attorney, Agent, or Firm* — Dickinson Wright PLLC

(57) ABSTRACT

A flush syringe for use in maintaining intravenous catheters, wherein the flush syringe can more efficiently and effectively flush the catheters by providing a pulsating, pulsatile, and/or pulsative flow of fluid that can be produced using momentum of the fluid moving. A steady force applied to a plunger while flushing can provide the pulsating, pulsatile, and/or pulsative flow of the fluid to the catheters.

17 Claims, 22 Drawing Sheets

200
245
240
244
220
210
230
241
242

(56) References Cited

U.S. PATENT DOCUMENTS

| | | | |
|---|---|---|---|
| 2011/0087194 | A1 | 4/2011 | Carpenter |
| 2013/0172811 | A1 | 7/2013 | Uber, III et al. |
| 2015/0320937 | A1 | 11/2015 | Kosinski et al. |
| 2016/0213834 | A1 | 7/2016 | Brady et al. |
| 2016/0310660 | A1 | 10/2016 | Burns et al. |
| 2017/0100576 | A1 | 4/2017 | Stout et al. |

* cited by examiner

PULSATILE OR RESONATING FLUSH SYRINGE

CROSS-REFERENCE TO RELATED APPLICATIONS

This application is a National Stage entry, under 35 U.S.C. § 371, of International Application PCT/US2019/015208, filed Jan. 25, 2019, which claims priority under 35 USC § 119(e) from U.S. Provisional Patent Application No. 62/622,907 filed on Jan. 28, 2018, the contents of which (including all attachments filed therewith) are hereby incorporated by reference in their entirety.

TECHNICAL FIELD

Generally, exemplary embodiments of the present disclosure relate to the fields of vascular access devices, and in particular flush devices for use in maintaining intravenous (IV) catheters.

BACKGROUND

In the example of medical applications, various procedures are used to flush IV catheters in order to prevent obstruction which is a potential source of infection, and/or clear bacteria to prevent bacterial colonization of IV catheters. Studies, such as "Pulsative Flushing As A Strategy To Prevent Bacterial Colonization Of Vascular Access Devices" by Agnes Ferroni et al. (Medical Devices: Evidence and Research 2014:7 379-383, Doverpress 2004) (the entire disclosures of which is incorporated herein by reference), have demonstrated that using pulsating flow, sometimes referred to as "start-stop" flushing, by alternatingly applying high and low force to the syringe plunger, is more than twice as effective at clearing bacteria from IV catheters compared to continuous (constant flow rate) flushing.

Conventional techniques include manually producing a pulsating flow from conventional flush syringe designs and typically involve the use of both hands to alternatingly apply high and low force to the syringe plunger. Other means of producing pulsatile flow from flush syringes are described in U.S. Pat. No. 8,491,537 and U.S. Published Patent Application Publication No. 20100076370 (the entire disclosures of both of which are incorporated herein by reference).

U.S. Pat. No. 8,491,537 describes a flush syringe assembly as illustrated in FIGS. 1A and 1B, which includes a syringe barrel 110 with an open proximal end 119 and a distal end 111 having a collar 121, a tip cap 124 to engage collar 121 a plunger rod 130 disposed within the syringe barrel 110, a stopper 160 attached to one end 133 of the plunger rod 130, a thumb press 170 attached to the second end of the plunger rod 130 and a pulse control element 190 disposed between the thumb press 170 and the plunger rod 130. A pulsing element 136 is provided as projections disposed along the length of the plunger rod 130 that engages with pulsing element 126 provided as projections disposed on interior surface of the syringe barrel 110, to cause pulsatile movement of the plunger rod 130 as it moves within the barrel 110 in at least the distal direction.

U.S. Publication No. 20100076370 describes other variations of the plunger rod and barrel designs, as well as in-line pulsing devices for generating a pressure pulse which provides turbulent flow for purging, such as those illustrated in: FIGS. 9-14 of U.S. Publication No. 20100076370, where in-line automatic pulsing device 310 comprises an upstream or proximal connection 320, into which liquid from a liquid source is provided, and an output port and connector 330 which may be connected to a downstream catheter system; FIGS. 15-17 where pinch or squeeze pump 410 comprises an upstream or proximal connection 420, into which liquid from a liquid source is provided, and an output port and connector 430 which may be connected to a downstream catheter system and FIGS. 18-20 where device 510, which provides manually, digitally generated controlled pressure pulses for purging catheter systems, comprises an upstream or proximal connection 520, into which liquid from a liquid source is provide, and an output port and connector 530 which may be connected to a downstream catheter system.

Both U.S. Pat. No. 8,491,537 and U.S. Publication No. 20100076370 describe embodiments where the pulsatile fluid flow can be produced by a mechanical interference and interaction between features on the syringe plunger rod and features on the syringe barrel, and/or an additional in-line pulsating device. Alternative implementations which may reduce an impact of syringe plunger on a clinician when perforating flushing operation, and/or avoid the use of an additional in-line device are desirable.

SUMMARY

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

As would be readily appreciated by skilled artisans in the relevant art, while descriptive terms such as "pulse", "pulsatile", "flow", "distal", "proximal", "flush", "syringe", "wheel", "vanes", "incline", "wall", "top", "side", "bottom" and others are used throughout this specification to facilitate understanding, it is not intended to limit any components that can be used in combinations or individually to implement various aspects of the embodiments of the present disclosure.

Exemplary embodiments of the present disclosure provide a flush syringe for use in maintaining intravenous catheters, which can more efficiently and effectively flush catheters by providing a pulsating, pulsatile, and/or pulsative flow of fluid rather than, for example, a constant flow. In an exemplary implementation, a pulsating flow is produced using the momentum of the moving fluid itself, rather than for example by a mechanical action of a syringe plunger. According to exemplary implementations, a clinician operating a syringe according to exemplary embodiments of the present disclosure can apply a steady force to the plunger while flushing and provide a pulsating flow of fluid to a catheter.

According to exemplary embodiments of present disclosure, a pulsatile flow can be produced by a flowing fluid causing a wheel with vanes disposed in the flowing fluid to rotate. In an exemplary implementation, the vanes can be non-inclined and a rotational velocity component in the fluid can be induced before the fluid strikes the non-inclined vanes. In another exemplary implementations, the vanes can be inclined and a rotational velocity component in the fluid can be induced by the vanes being inclined. In yet another exemplary implementation, configuration of inclined vanes on a wheel can resemble that of a turbine or a pinwheel.

In still further exemplary implementations of the embodiments of the present disclosure. a rotating wheel can comprise one or more openings, which alternatingly cover and uncover exit orifices downstream of the wheel, for example causing the fluid flow to start and stop at each exit orifice, leading to a pulsatile flow through a syringe tip.

According to yet further exemplary embodiments of the present disclosure, pulsatile flow can be caused by the motion of fluid being infused at the tip of the syringe barrel such that pressure waves in the fluid can be damped for example before reaching the syringe plunger, and the users thumb or finger. Exemplary non-limiting advantages that may be achieved reduce sensation to a clinician that may be caused by prior implementations having possible hammering impacts of a syringe plunger interacting with alternating features on the syringe barrel or other components.

According to another exemplary embodiment of the present disclosure, a flush syringe is configured to produce pulsating or pulsatile flow to an IV catheter for a more efficient flushing using resonance of one or more members to create the pulsating flow. In an exemplary implementation, an underlying technical principle includes resonance of a flexible body due to the interaction between pressure differentials and turbulence as fluid flows around the body, and the flexibility of the body allowing it to distort due to variations in pressure and turbulent velocity eddies along its surface. An exemplary non-limiting advantage of provided exemplary implementations is use of fewer total components, and lack of moving pans, which could require tighter tolerances.

In an exemplary implementation, one or more members can be structurally flexible and/or disposed inside a flush syringe. An exemplary implementation the present disclosure provides an additional component to an existing flush syringe design, where such component can flex and be fixedly disposed relative to a mating components, or an attachment point, of a flush syringe. Exemplary non-limiting advantages include enabling potentially looser tolerances, further reducing manufacturing costs.

In an exemplary implementation of certain embodiments of the present disclosure, a pulsating fluid flow is produced from resonance caused by the interaction of one or more flexible members, with fluid flowing through the syringe into the catheter. The resonance of the flexible member alternatingly disrupts or restricts the fluid flow, creating a pulsatile type flow profile (varying pressure/velocity in the flow) beneficial to improve flushing. Alternately, in an exemplary implementation, the resonance could create pressure waves in the flow without disrupting or restricting the flow (such as when sound pressure waves move through liquids).

An exemplary implementation of embodiments of the present disclosure provides a resonant component comprising a relatively thin, wide tube that is nominally closed. Fluid being expelled from the flush syringe passes through this tube, causing the walls of the tube to alternatingly open and close against each other in a "flapping" manner. In an exemplary implementation, resonance of the walls of a thin-walled tube against each other produces a pulsatile flow exiting the syringe. In a non-limiting example, an operational mechanism is analogous to a "buzzing" of a balloon neck when air is released therefrom.

Another exemplary implementation of embodiments of the present disclosure provides a resonant component comprising a long, slender tube through which fluid being expelled from the flush syringe flows. In an exemplary implementation, at least a portion of, or the entire, tube whips around due to the exit velocity of fluid at the tip of the tube. In a non-limiting example, an operational mechanism is analogous to a fire hose (or other high-pressure hose) whipping around when high-velocity fluid flows therethrough.

Yet another exemplary implementation of embodiments of the present disclosure provides a resonant component comprising a relatively thin, wide, "ribbon-like" member over which fluid being expelled from the flush syringe passes. In an exemplary implementation, fluid does not flow through the resonant member but rather flow around it. In a non-limiting example of an operation, fluid flowing over the surfaces of the ribbon-like member causes it to "flap", alternatingly closing off fluid flow on one side or the other of the member as it alternatingly touches opposing syringe tip walls (or other walls of the syringe body). In a non-limiting example, an operational mechanism is similar to a flag flapping in a strong wind, or a reed vibrating in a wild animal call or wind instrument.

According to embodiments of the present disclosure, a resonating member is configures to avoid tearing, or become disconnected, so as not to block the fluid path of the catheter.

Exemplary embodiments of the present disclosure can provide a flexible member that would only resonate across a certain range of fluid velocities. Exemplary non-limiting advantages allow a clinician to depress the syringe plunger either faster (for example with more force) or slower (for example with less force) to avoid the range of fluid velocities producing resonance and pulsatile flow, for example if a clinician does not desire to administer pulsatile flow to the catheter.

BRIEF DESCRIPTION OF THE DRAWINGS

Referring now to the drawings, wherein like reference numerals designate identical or corresponding parts throughout the several views, embodiments of the present disclosure are described as follows.

DETAILED DESCRIPTION OF THE EXEMPLARY EMBODIMENTS

The matters exemplified in this description are provided to assist with a comprehensive understanding of exemplary embodiments with reference to the accompanying drawing figures. Accordingly, those of ordinary skill in the art will recognize that various changes and modifications of the exemplary embodiments described herein can be made within the scope of appended claims without departing from their full scope and equivalents. Also, descriptions of well-known functions and constructions are omitted for clarity and conciseness. Likewise, certain naming conventions, labels and terms as used in the context of the present disclosure are non-limiting and provided only for illustrative purposes to facilitate understanding of exemplary implementations of the exemplary embodiments.

Figure 1A:
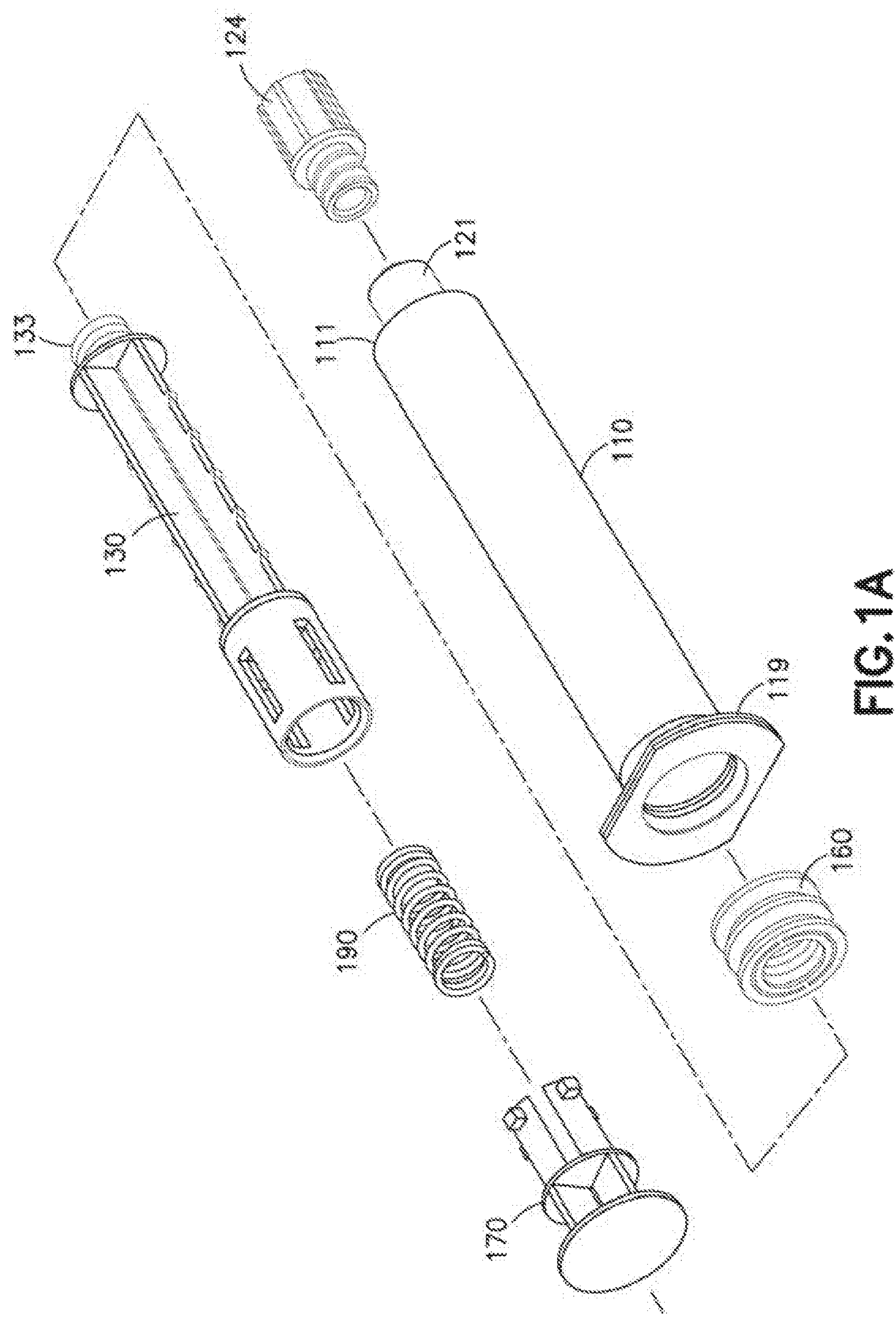
FIGS. 1A and 1B illustrate an example of a flush syringe assembly.
Figure 1B:
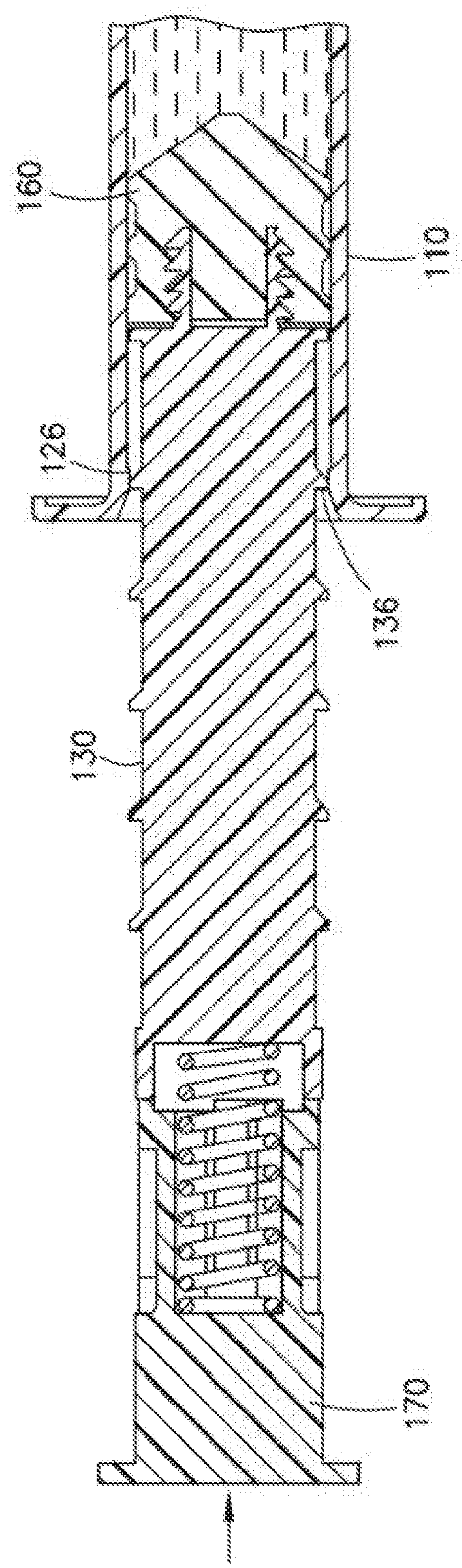
Figure 2A:
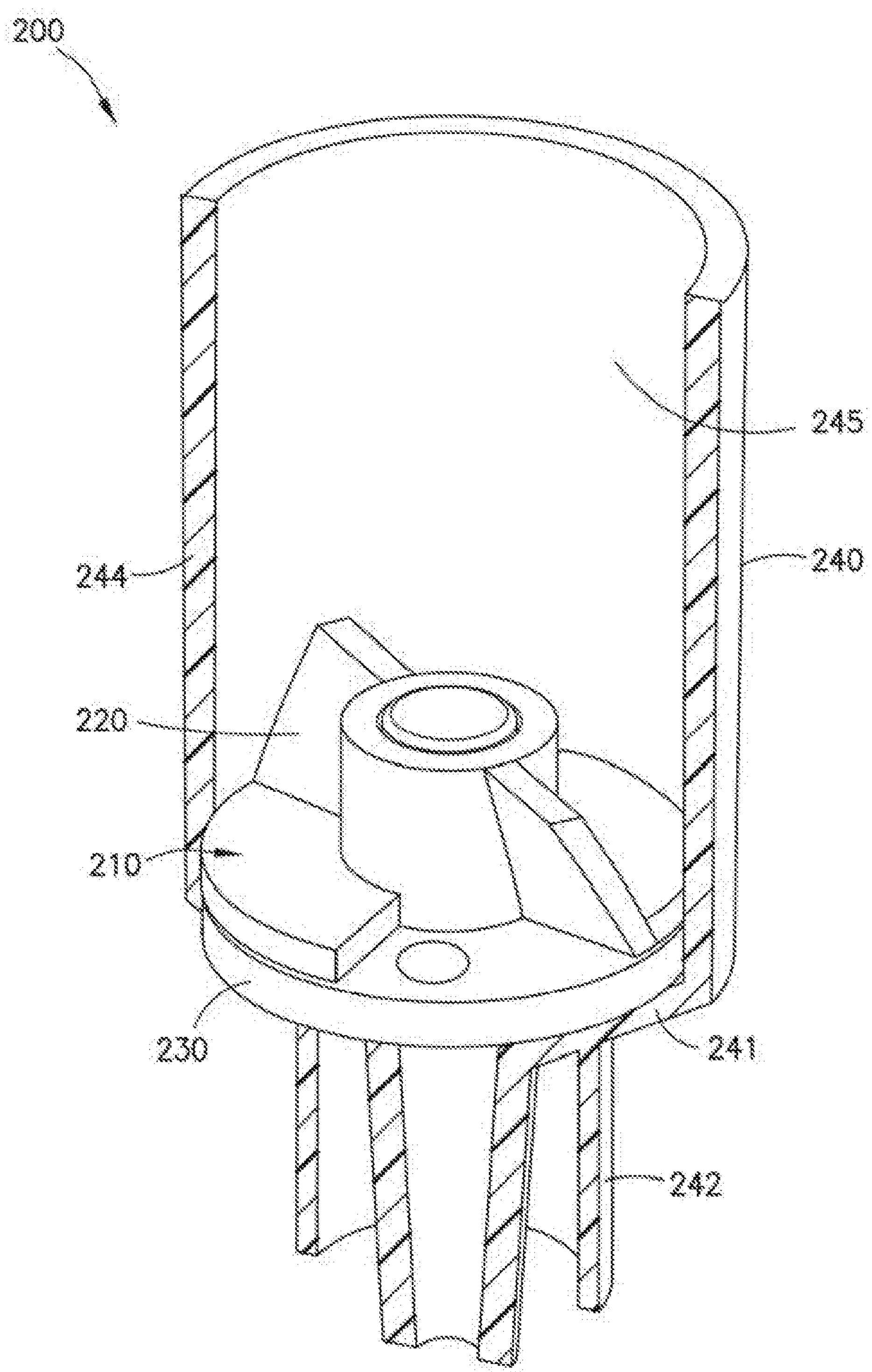
FIGS. 2A, 2B, 2C, 2D, 2E, 2F, and 2G illustrate various views of a syringe barrel including a flushing mechanism and various components thereof according to exemplary embodiment of the disclosure.
Figure 2C:
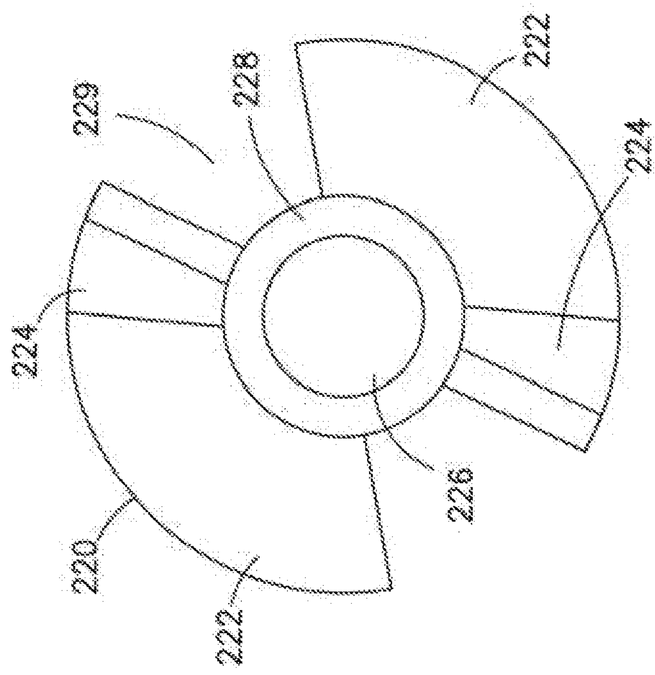
Figure 2B:
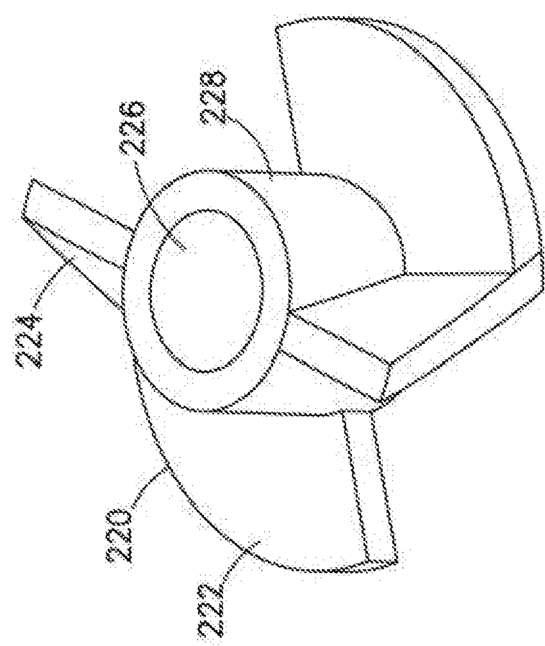
Figure 2D:
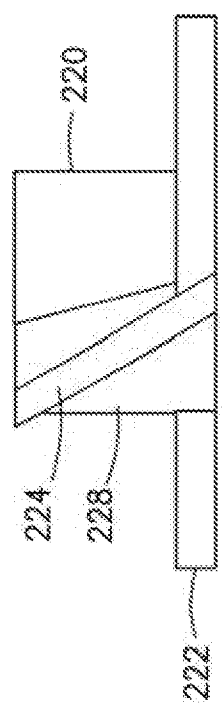
Figure 2F:
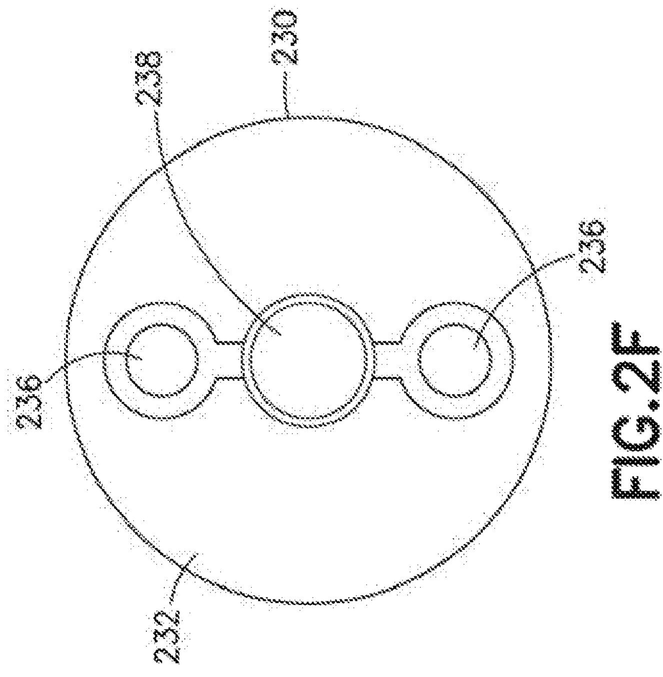
Figure 2E:
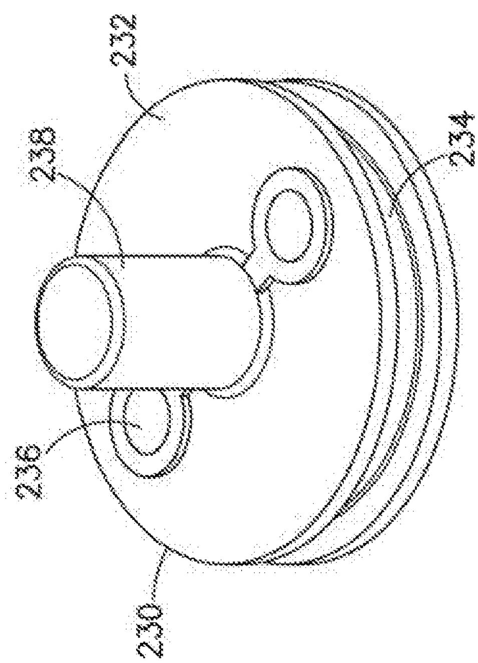
Figure 2G:
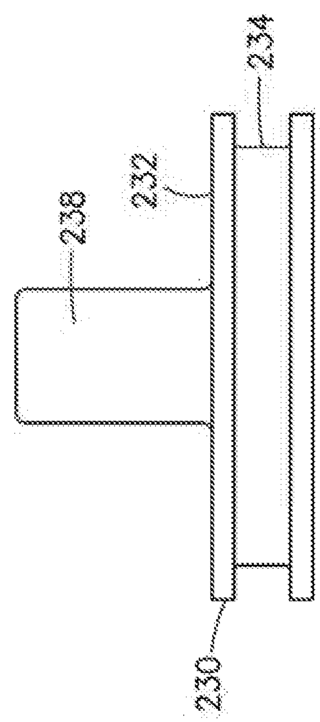
Figure 3A:
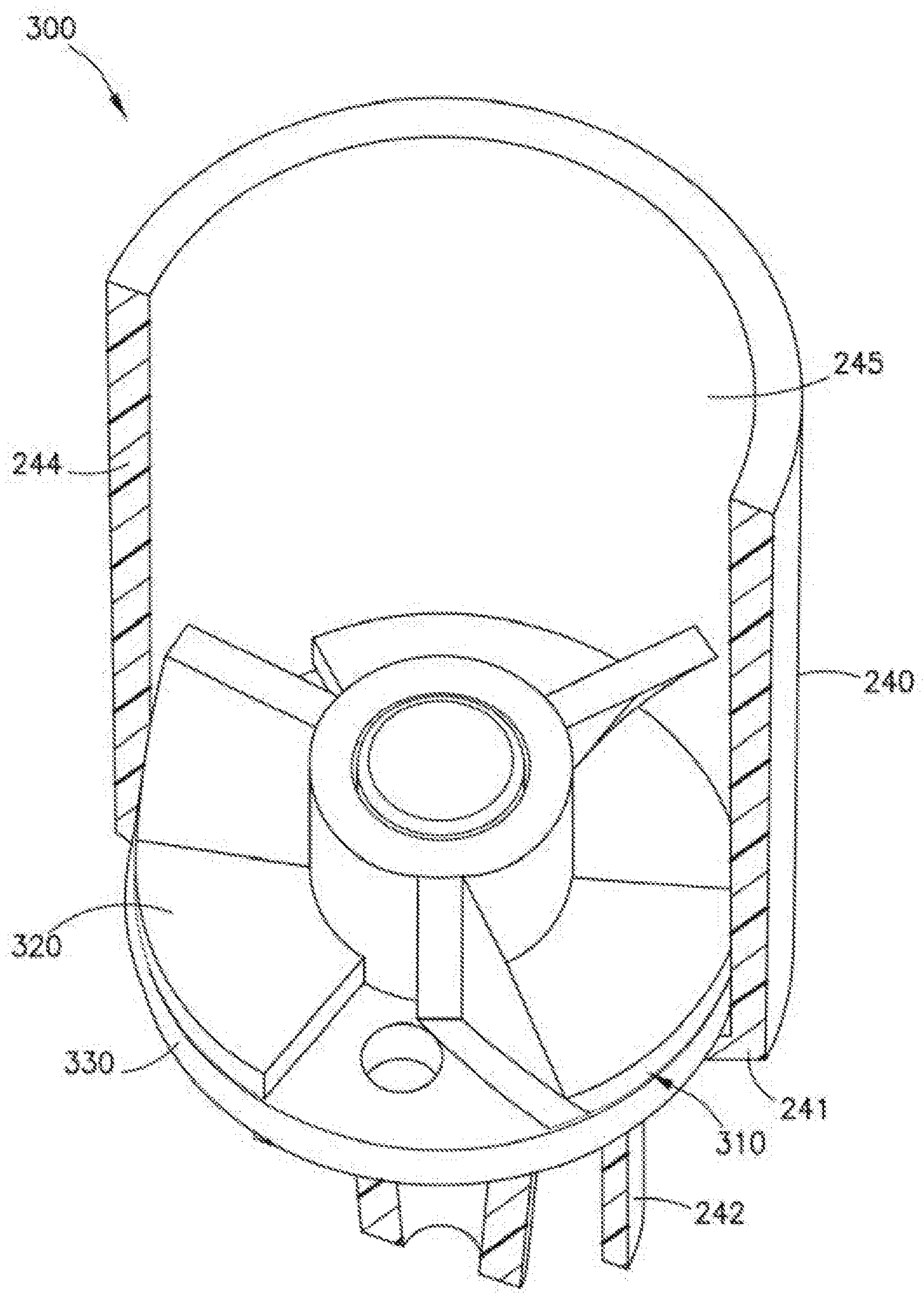
FIGS. 3A, 3B, 3C, 3D, 3E, 3F, and 3G illustrate various views of a syringe barrel including a flushing mechanism and various components thereof according to another exemplary embodiment of the disclosure.
Figure 3B:
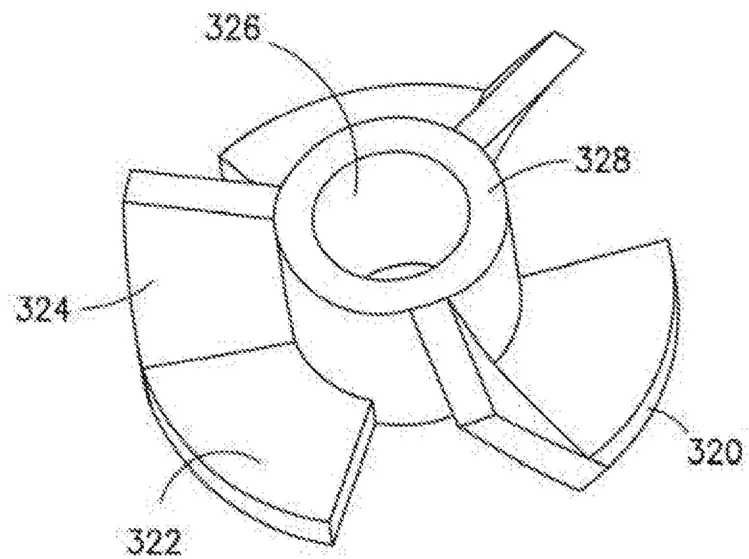
Figure 3C:
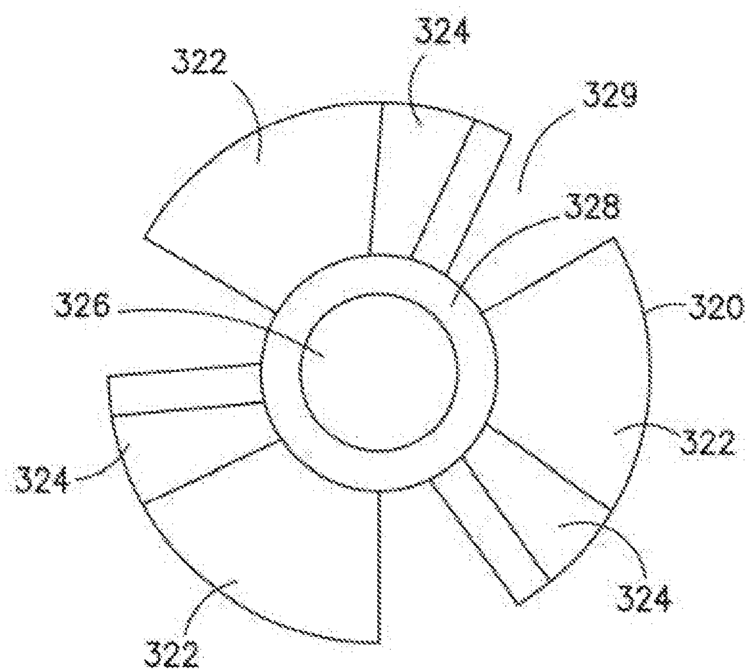
Figure 3D:
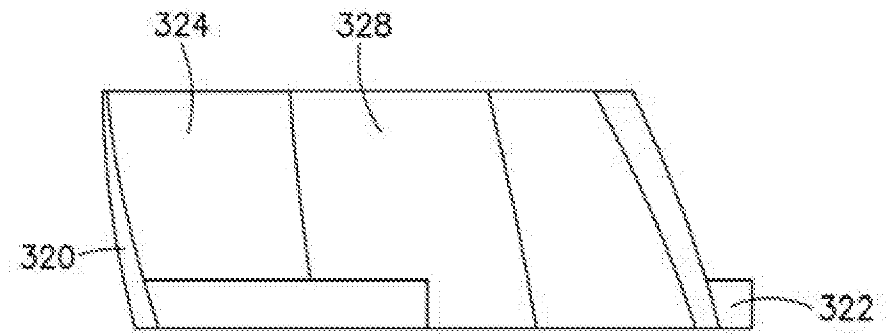
Figure 3E:
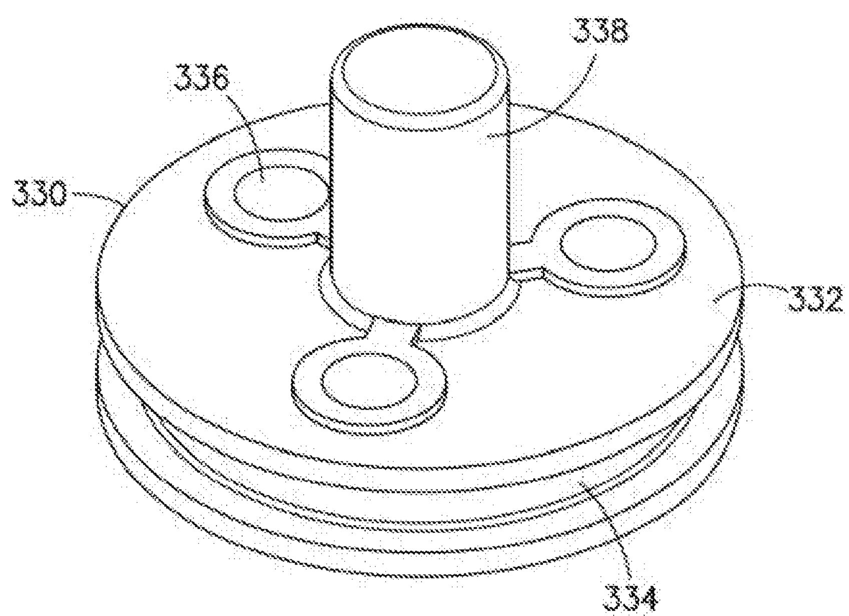
Figure 3F:
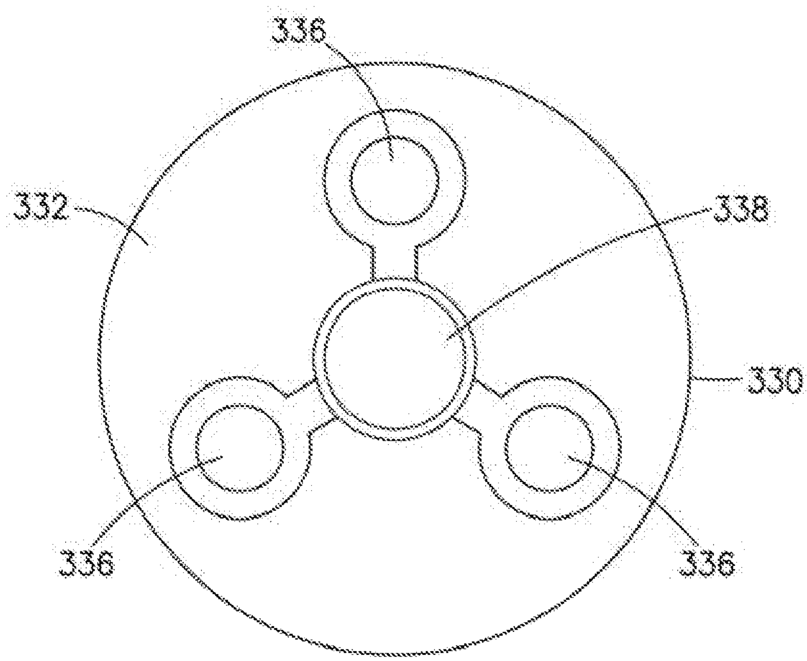
Figure 3G:
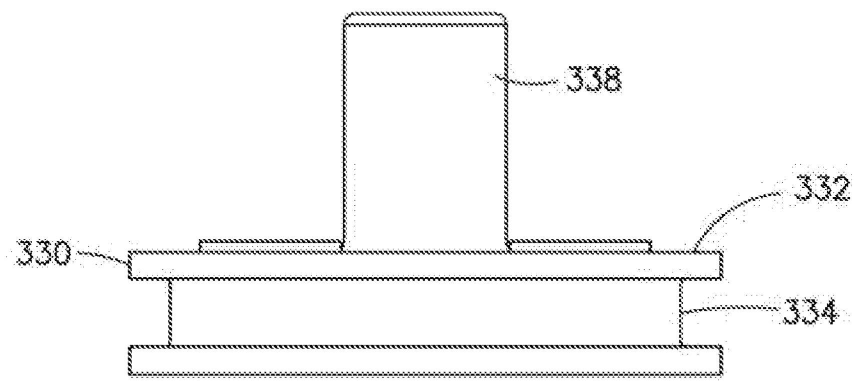
Figure 4A:
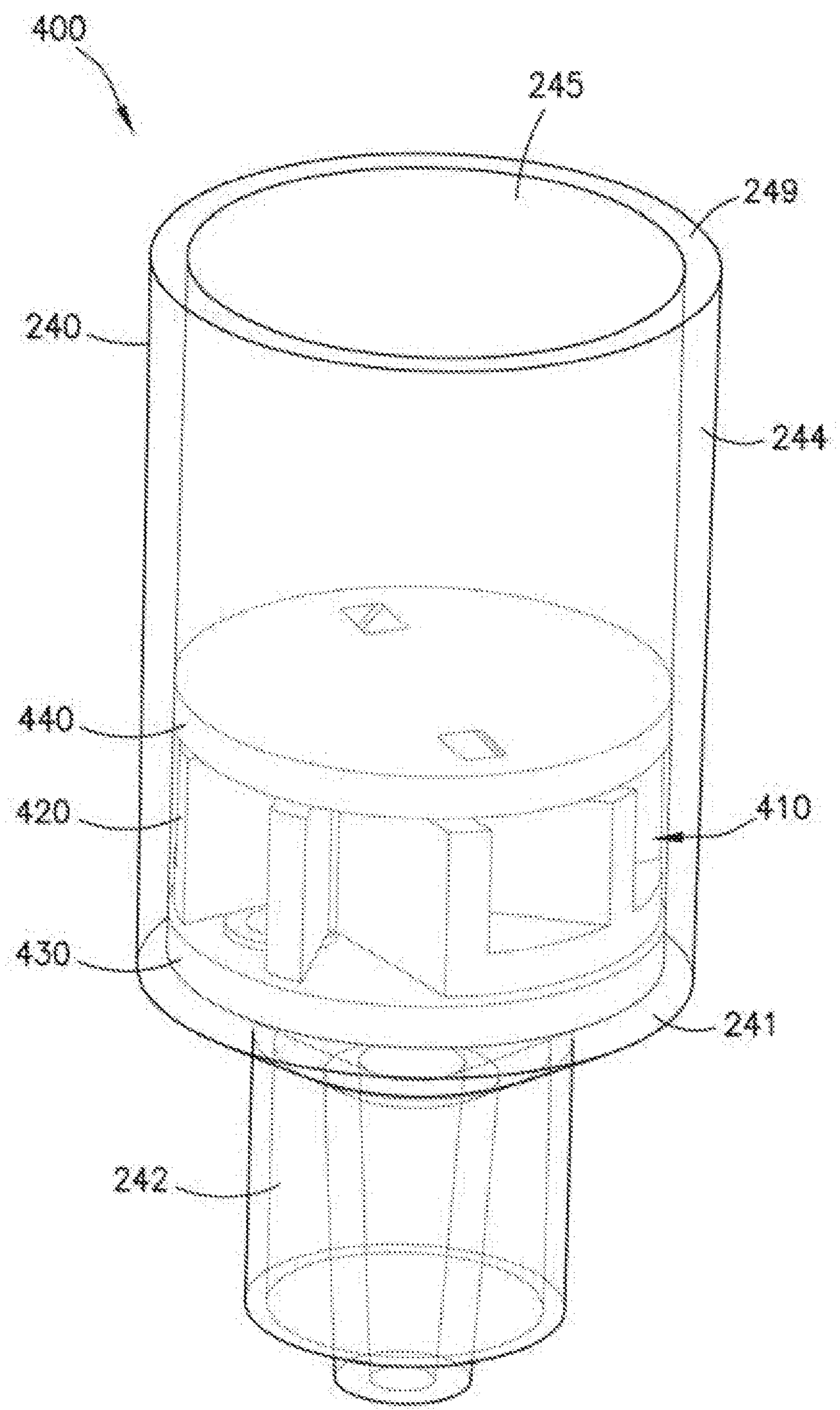
FIGS. 4A, 4B, 4C, 4D, 4E, 4F, 4G, 4H, 4I, and 4J illustrate various views of a syringe barrel including a flushing mechanism and various components thereof according to yet another exemplary embodiment of the disclosure.
Figure 4C:
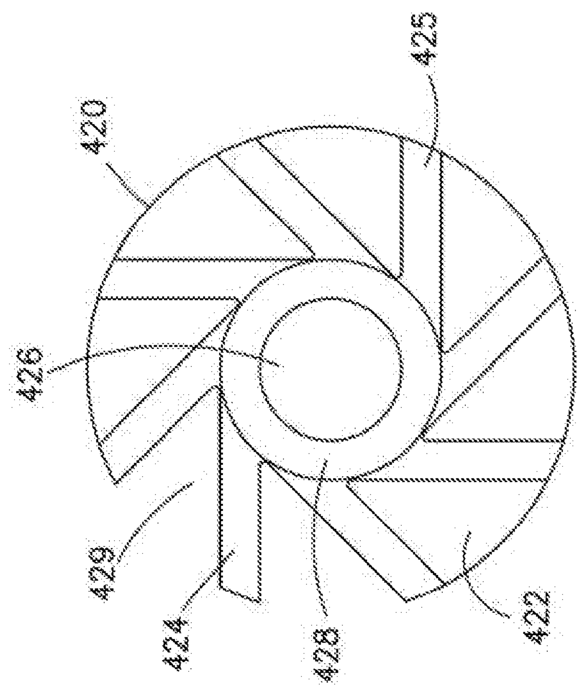
Figure 4B:
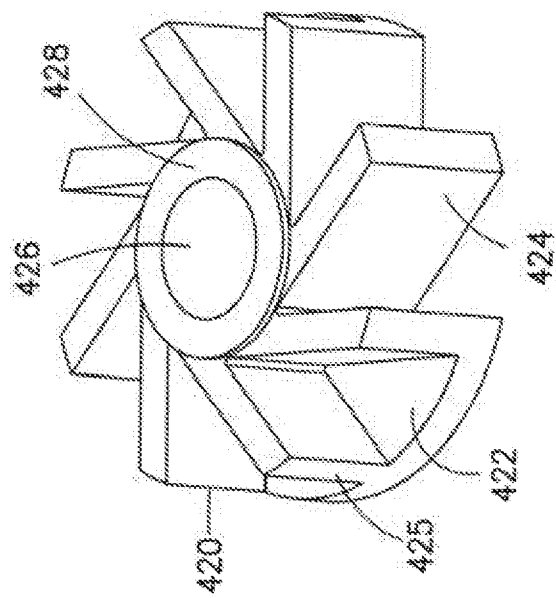
Figure 4D:
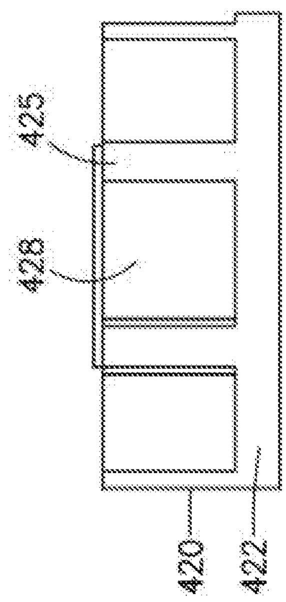
Figure 4F:
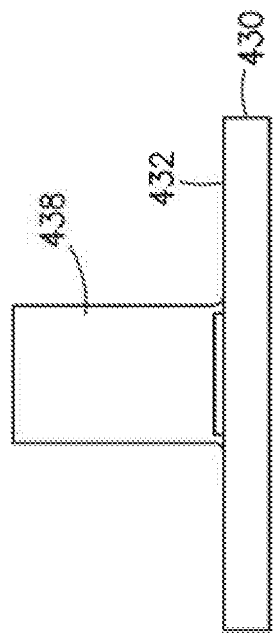
Figure 4G:
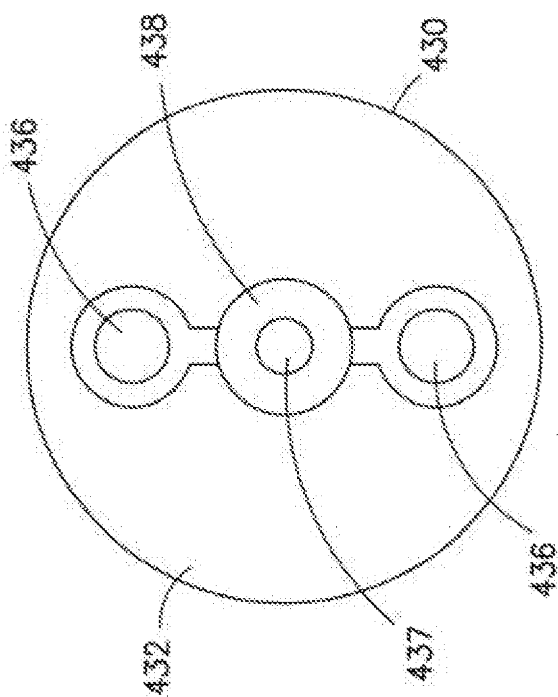
Figure 4E:
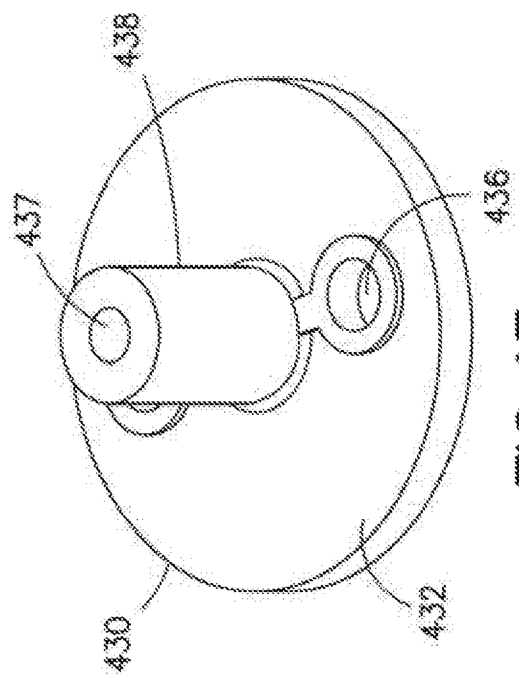
Figure 4I:
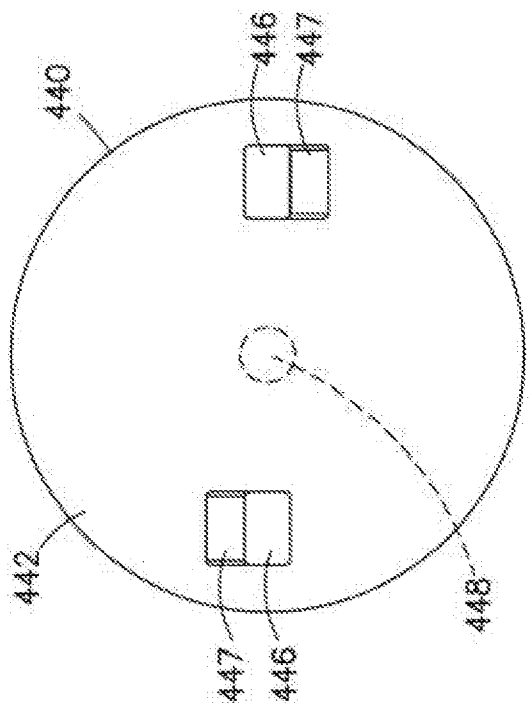
Figure 4H:
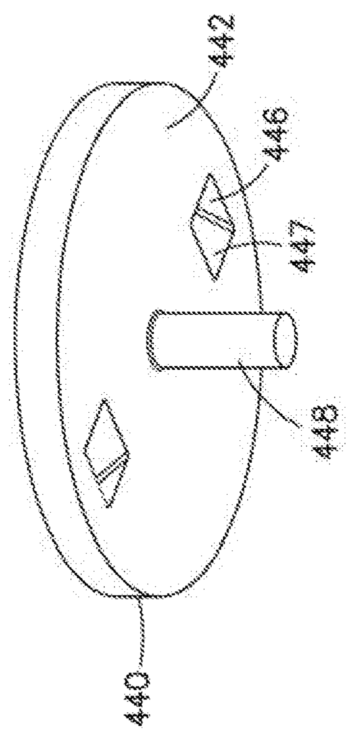
Figure 4J:
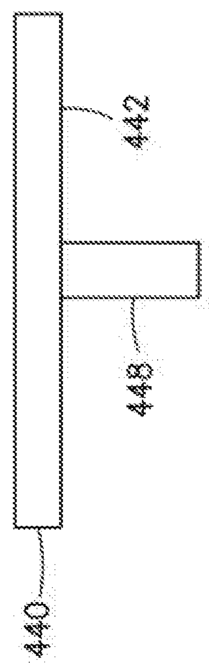
Figure 5A:
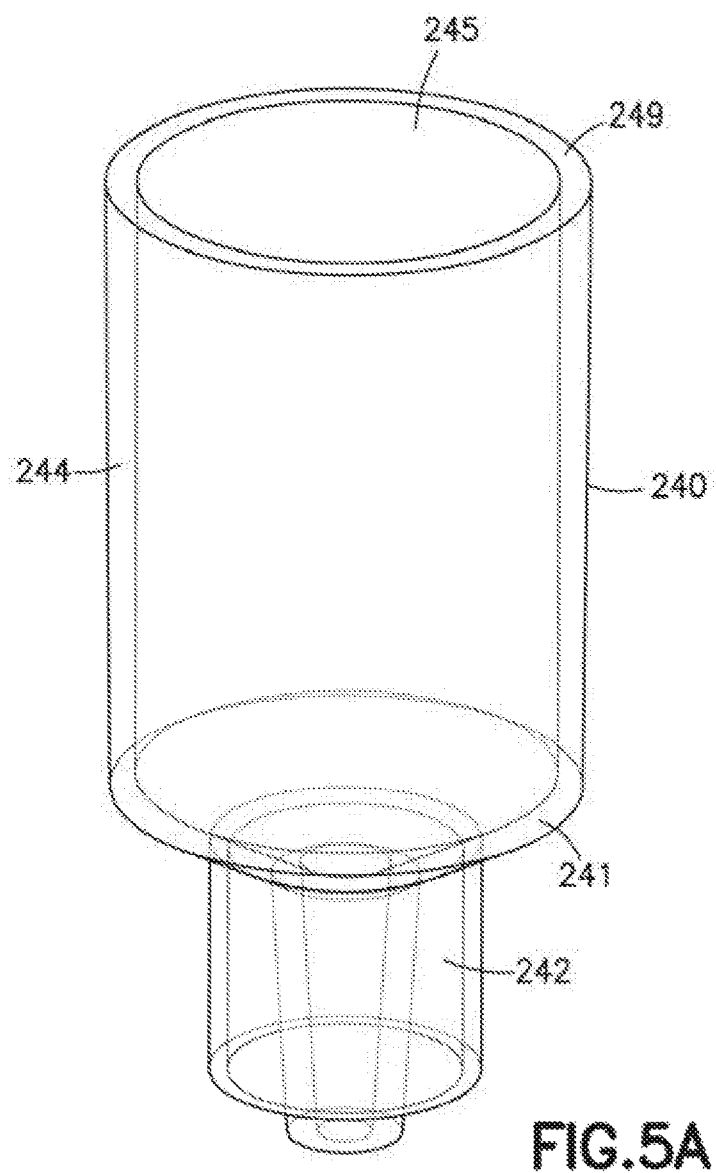
FIG. 5A illustrates perspective view of a syringe barrel comprising a flushing mechanism, or combination of mechanisms, according to exemplary embodiments and/or implementations of the present disclosure.

Referring to FIGS. 2A-2G and 3A-3G, according to exemplary embodiments of the present disclosure a flushing syringe 200/300 comprises a flushing mechanism 210/310 disposed in syringe barrel 240. As illustrated in the example of FIG. 5A, a syringe barrel 240 comprises a sidewall 244 defining an essentially cylindrical chamber 245 with an open proximal end (not shown) and a distal end 241 having a syringe tip 242, where a plunger rod (not shown) disposed within syringe barrel 240 produces flow of fluid within chamber 245 toward distal end 241 and out of syringe tip 242 when pushed, for example by a clinician, in the direction of distal end 241.

In an exemplary implementation, flushing mechanism 210/310 comprises an orifice plate 230/330 disposed downstream, or distally, of a rotating wheel 220/320. Optionally, orifice plate 230/330 can be friction fitted with chamber 245. In an exemplary configuration, plate 230/330 comprises a platen 232/332 with a pin 238/338 extending therefrom around which wheel 220/320 can rotate. In an exemplary implementation, platen 232/332 is essentially circular with pin 238/338 extending essentially perpendicular thereto. Plate 230/330 further comprises one or more orifices 236/336 (two orifices 236 in the example of FIGS. 2E-2G, and three orifices 336 in the example of FIGS. 3E-3G) in platen 232/332, such as exit orifices for fluid flowing therethrough from chamber 245 out of tip 242. Plate 230/330 can be disposed within chamber 245 in close proximity to distal end 241 and can be permanently and/or removably fixed, rotationally and/or axially, within chamber 245 for example by platen 232/332 with respect to interior surface of sidewall 244, and/or bottom portion of distal end 241.

Figure 5B:
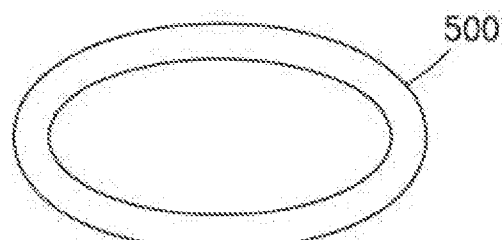
FIG. 5B illustrates perspective view of a ring, such as an O-ring, which can be utilized to secure a flushing mechanism, or combination of mechanisms, within a syringe barrel according to exemplary embodiments and/or implementations of the present disclosure
Figure 6A:
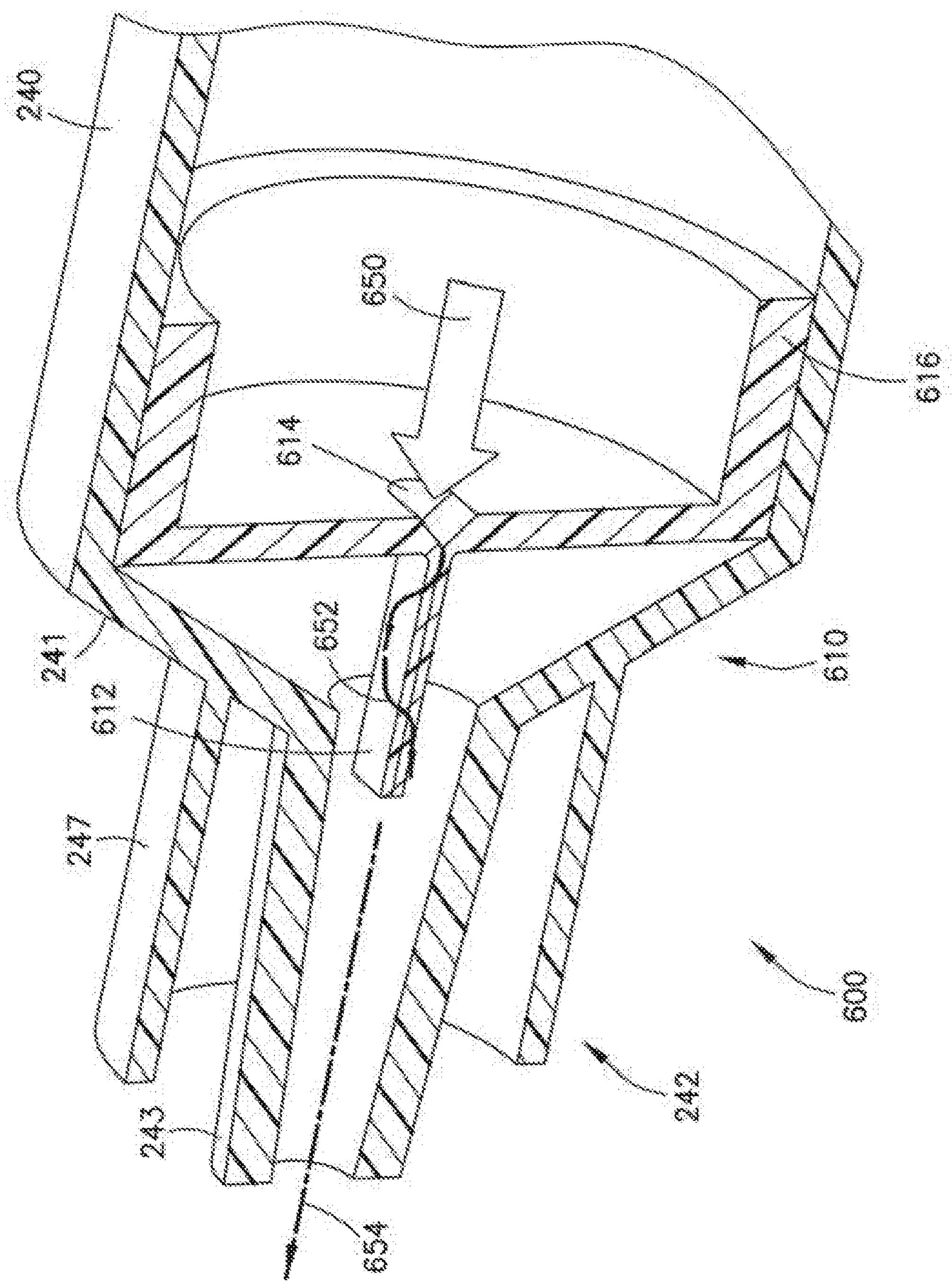
FIGS. 6A, 6B, 6C, and 6D illustrate various views of a syringe barrel including a flushing mechanism and various components thereof according to an alternative exemplary embodiment of the disclosure.
Figure 6B:
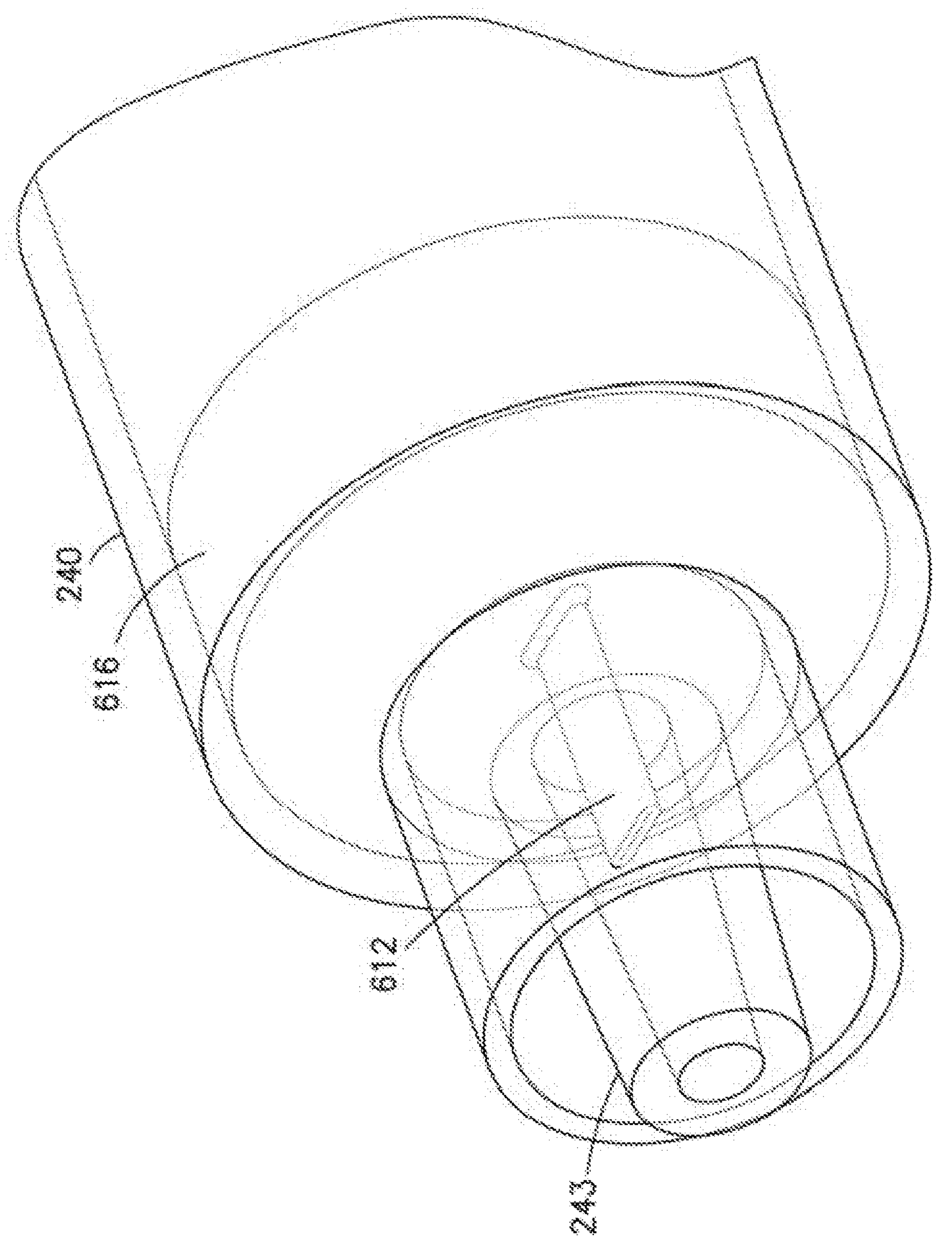
Figure 6C:
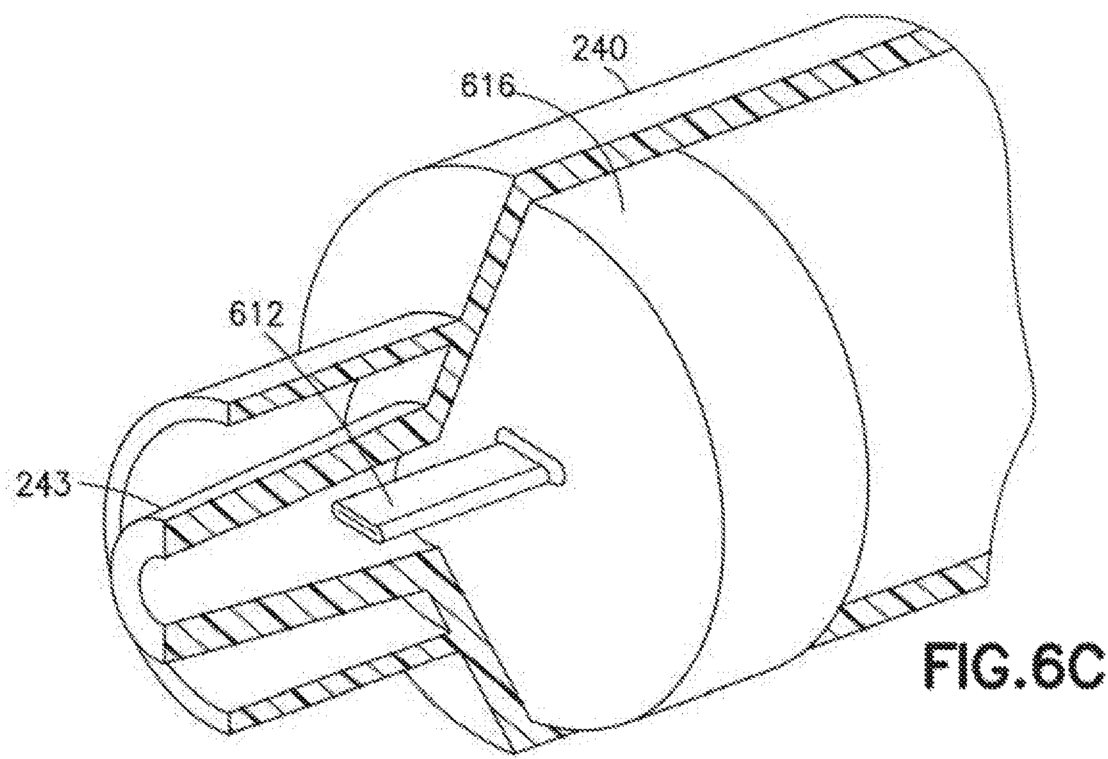
Figure 6D:
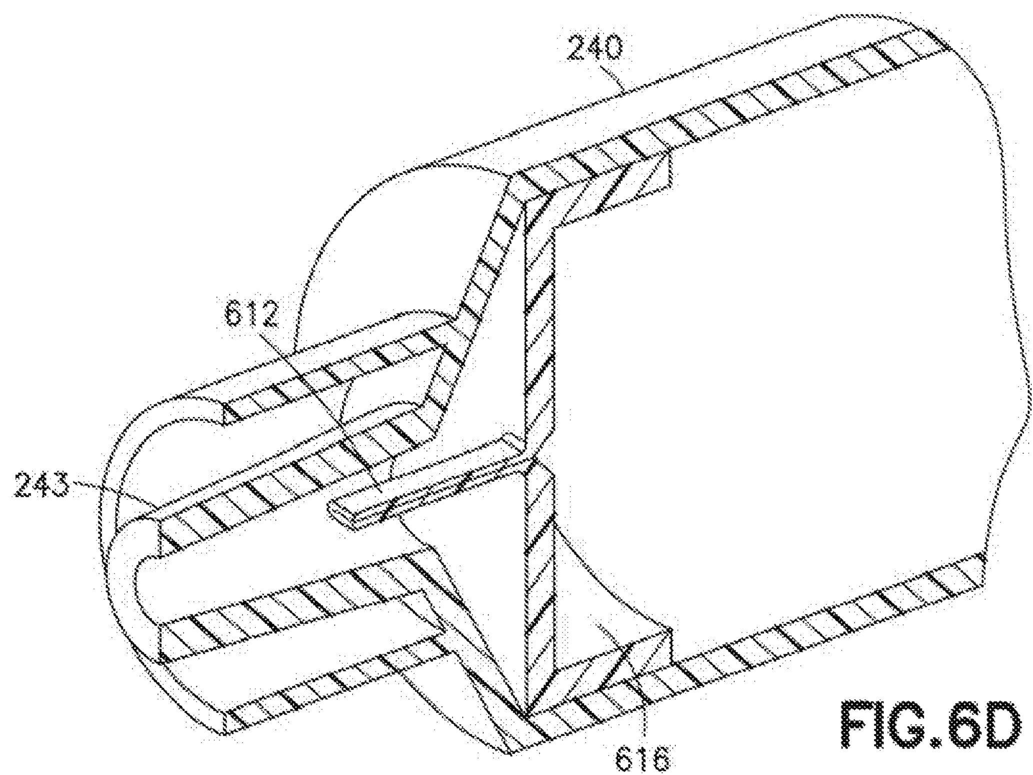
Figure 7A:
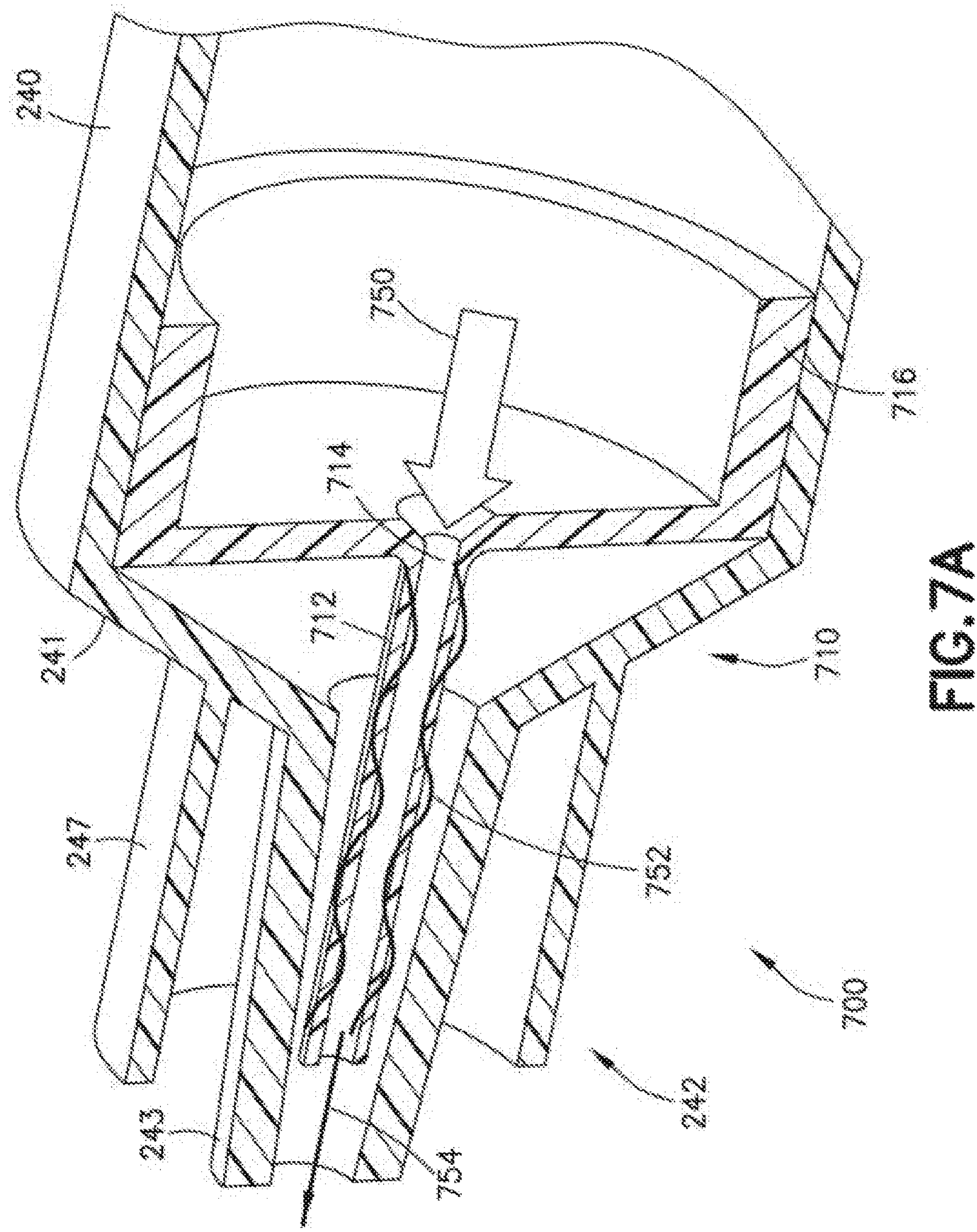
FIGS. 7A, 7B, 7C, and 7D illustrate various views of a syringe barrel including a flushing mechanism and various components thereof according to another alternative exemplary embodiment of the disclosure.
Figure 7B:
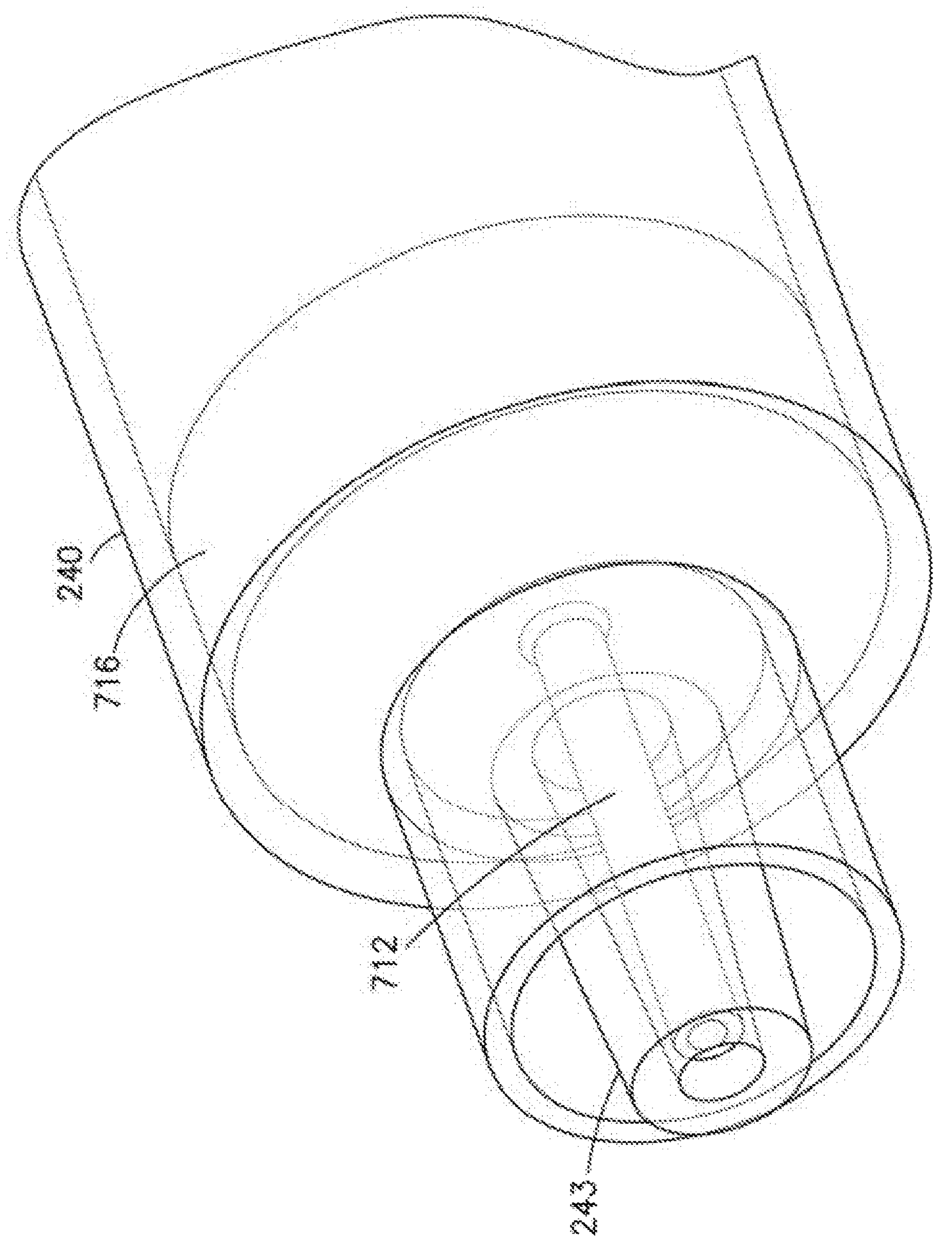
Figure 7C:
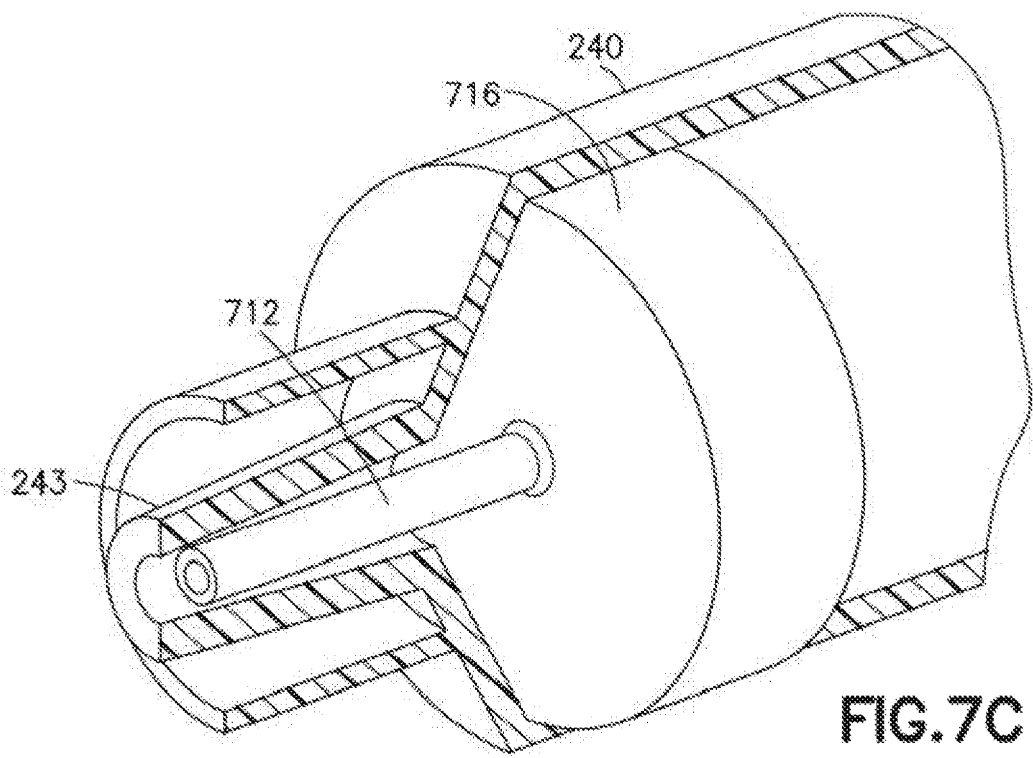
Figure 7D:
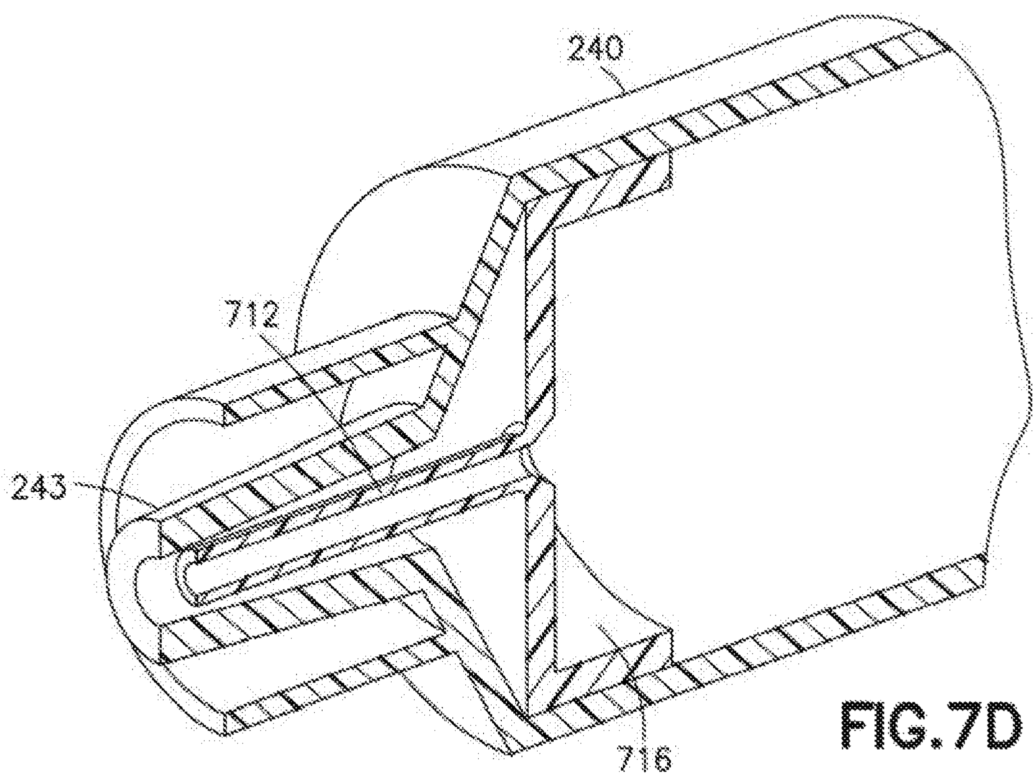

In an exemplary implementation, plate 230/330 comprises a grove 234/334 in an outer perimeter of platen 232/332 for accommodating, for example a rubber, plastic or other flexible or compressible, O-ring, such as an O-ring 500 illustrated in FIG. 5B, to facilitate friction lit of plate 230/330 with respect to interior surface of side wall 244. In an exemplary implementation plate 230/330 can be positioned within chamber 245 to facilitate a fluid-tight seal of plate 230/330 with respect to interior sidewall 244. In an exemplary implementation, the entire structure of plate 230/330 can be unitary, for example formed by injection molding In an exemplary implementation, wheel 220/320 comprises a platen 222/322 having one or more inclined vanes 224/324, for example at a non-ninety-degree angle with respect to platen 222/322 (two vanes 224 in the example of FIGS. 2B-2D, and three vanes 324 in the examples of FIGS. 3B-3D) and hub 228/328 extending therefrom. In an exemplary implementation, hub 228/328 is essentially centrally located on platen 222/322 and extend essentially perpendicular thereto. Hub 228/328 and platen 222/322 have an essentially cylindrical opening 226/326 extending therethrough for receiving pin 238/338. Platen 222/322 comprises one or more openings, for example cut-outs, 229//329 (two opening 229 in example of FIGS. 2B-2D, and three openings 329 in the example of FIGS. 38-3D). In an exemplary implementation, the entire structure of wheel 220/320 can be unitary, for example formed by injection molding.

In a further exemplary implementation, wheel 220/320 can be fixed to plate 230/330, for example by snap-fit of pin 238/338 within hub 228/328, to restrict axial movement of wheel 220/230 with respect to plate 230/330 while allowing free rotational movement of wheel 220/230 with respect to plate 230/330.

In an exemplary embodiment of flush syringe and flushing mechanism 210/310 illustrated in FIGS. 2A-2G and 3A-3G, pulsatile flow can be produced by a flowing fluid in chamber 245 causing a wheel 220/320 with vanes 224/324 disposed in the flowing fluid to rotate with respect to plate 220/320 such that rotational velocity component in the fluid can be induced by the vanes 224/324 being inclined. In an exemplary implementation, configuration of inclined vanes 224/324 on a wheel 220/320 can resemble that of a turbine or a pinwheel. Rotating wheel 220/320 comprise one or more openings 229/239, which alternatingly cover and uncover exit orifices 236/336 of plate 230/330 downstream of the wheel 220/320, for example causing the fluid flow to start and stop at each exit orifice 236/336, leading to a pulsatile flow through a syringe tip 242.

Referring to FIGS. 4A-4J, according to exemplary embodiments of the present disclosure a flushing syringe 400 comprises a flushing mechanism 410 disposed in syringe barrel 240. In an exemplary implementation, flushing mechanism 410 comprises an orifice plate 430 disposed downstream, or distally, of a rotating wheel 420, which is disposed downstream, or distally, of a static plate 440.

In an exemplary configuration, plate 430 comprises a platen 432 with a pin 438 extending therefrom around which wheel 420 can rotate. In an exemplary implementation, platen 432 is essentially circular with pin 438 extending essentially perpendicular thereto. Plate 430 further comprises one or more orifices 436 in platen 432, such as exit orifices for fluid flowing therethrough from chamber 245 out of tip 242. Plate 430 can be disposed within chamber 245 in close proximity to distal end 241 and can be permanently and/or removably fixed, rotationally and/or axially, within chamber 245 for example by platen 432 with respect to interior surface of sidewall 244, and/or bottom portion of distal end 241. In an exemplary implementation, the entire structure of plate 430 can be unitary, for example formed by injection molding.

In an exemplary implementation, wheel 420 comprises a platen 422 having one or more non-inclined vanes 424, which can be essentially perpendicular to platen 422, and hub 428 extending therefrom. In an exemplary implementation, hub 428 is essentially centrally located on platen 422 and extend essentially perpendicular thereto. Hub 428 and platen 422 have an essentially cylindrical opening 426 extending therethrough for receiving pin 438. Platen 422 comprises one or more openings, for example cut-outs, 429. In an exemplary implementation, the entire structure of wheel 420 can be unitary, for example formed by injection molding.

In an exemplary configuration, plate 440 comprises a platen 442 with a pin 448 extending therefrom. In an exemplary implementation, pin 438 of plate 430 comprises a hollow cylindrical opening 437 for receiving pin 448 therein. In an exemplary implementation, platen 442 is essentially circular with pin 448 extending essentially perpendicular thereto. Plate 440 further comprises one or more orifices 446 in platen 442 having an inclined wall 447, such as exit orifices, for fluid flowing therethrough from chamber 245 and impacting one or more vanes 424 at a non-zero angle. In an exemplary implementation, plate 440, instead of or as well as plate 430, can be permanently and/or removably fixed, rotationally and/or axially, within chamber 245 for example by platen 442 with respect to interior surface of sidewall 244, and/or bottom portion of distal end 241. In an exemplary implementation, the entire structure of plate 440 can be unitary, for example formed by injection molding.

In an exemplary implementation, plate 430 and/or 440 can comprise a grove (not show, but see examples of FIGS. 2E-2G and 3E-3G) in an outer perimeter of platen 442 for accommodating, for example a rubber, plastic or other flexible or compressible, O-ring, such as an O-ring 500 illustrated in FIG. 5B, to facilitate friction fit of plate 430 and/or 440 with respect to interior surface of side wall 244. In an exemplary implementation plate 430 and/or 440 can be positioned within chamber 245 to facilitate a fluid-tight seal of plate 430 and/or 440 with respect to interior sidewall 234.

In a further exemplary implementation, wheel 420 can be fixed between plates 420 and 440, for example by snap-fit of pin 448 within hollow pin 438, to restrict axial movement of wheel 420 with respect to plate 430 and/or 440 while allowing free rotational movement of wheel 420 with respect to plate 430 and 440.

In an exemplary embodiment of flush syringe and flushing mechanism 410 illustrated in FIGS. 4A-4J, pulsatile flow can be produced by a flowing fluid in chamber 245 through orifices 446 such that rotational velocity component in the fluid can be induced by inclined 447 causing heel 420 with vanes 424 disposed in the fluid flowing through orifices 446 to rotate with respect to plate 420. Rotating wheel 420 comprises one or more openings 429, which alternatingly cover and uncover exit orifices 436 of plate 430 downstream of the wheel 420, for example causing the fluid flow to start and stop at each exit orifice 436, leading to a pulsatile flow through a syringe tip 242.

An exemplary embodiment of the present disclosure with lower manufacturing cost can provide a wheel with inclined vanes (a turbine), manufactured by molding. As noted herein, using a wheel with inclined vanes would reduce the total number of components required to create the pulsatile flow—one rotating wheel/turbine, and one orifice plate downstream of the wheel, which would include a pin around which the wheel could rotate, as illustrated for example in FIGS. 2A-2G and 3A-3G.

An exemplary embodiment of the present disclosure can be configured to have the lowest "stack height" of the pulsatile flow mechanism, to minimize the additional size and material of the flush syringe, and to minimize the volume of fluid remaining in the syringe and not infused when the plunger reaches the pulsating flow mechanism, as illustrated for example in FIGS. 2A-2G, 3A-3G, and 4A-4J where pulsatile flow mechanism 210, 310, 410 can be disposed at a distal part of syringe barrel in close proximity to syringe tip 242.

In an exemplary implementation, rotational flow could also be induced in the fluid before it exits the tip of the flush syringe. In yet further exemplary implementation, rotational component of the fluid flow may persist until it reaches the IV catheter, and this rotational component of the fluid flow may assist in flushing blood or other non-desirable fluids from areas in the catheter fluid path that are difficult to flush with a constant, non-rotating flow (such as sharp inside corners).

Alternative embodiments oldie present disclosure using fluid momentum to produce pulsatile flow utilize a resonating (flapping, fluttering) flexible valve, which can flutter or resonate across a range of fluid velocities.

Referring to FIGS. 6A-6D, an exemplary alternative implementation of embodiments of the present disclosure provides a syringe 600 having at a distal end 241 of syringe barrel 240 a resonant flushing component 610 comprising a flapper, for example a relatively thin, wide tube, 612 that is nominally closed disposed on a flapper support structure 616. As illustrated in more detail, syringe tip syringe 242 includes a tip 243 within a luer lock collar 247. Fluid 650 being expelled from barrel 240 of the flush syringe 600 by a moving plunger (not shown) flows into narrow slit 614 in flapper 612, passes 652 through flapper 612, causing the walls of the flapper 612 to alternatingly open and close against each other in a "flapping" manner. For example, low pressure from fluid velocity causes flapper walls to move toward each other to close slit 614. In an exemplary implementation, resonance of the walls of a thin-walled tube against each other produces a pulsatile flow 654 exiting the syringe 600 at tip 243 thereof. In a non-limiting example, component 610 can be produced as a unitary component and secured axially and rotationally inside chamber 245 of barrel 240 at a distal end 241 thereof such that at least a portion of flapper 612 extends into tip 243 of syringe 600.

Referring to FIGS. 7A-7D, another exemplary alternative implementation of embodiments of the present disclosure provides a syringe 700 having at a distal end 241 of syringe barrel 240 a resonant flushing component 710 comprising a long, slender tube 712 with an opening 714 disposed on a tube support structure 716. Fluid 750 being expelled from barrel 240 of the flush syringe 700 by a moving plunger (not shown) flows into opening 714 in tube 712, and flows 752 through tube 712. In an exemplary implementation, at least a portion of, or the entire, tube 712 whips around due to the exit velocity of fluid at the tip of the tube 712. For example, fluid exiting tip of tube 712 creates a compressive recoil force on tube 712, and tube 712 becomes unstable under compressive recoil forces 752 and "whips" periodically kinking to create a pulsate flow 754. In a non-limiting example, component 710 can be produced as a unitary component and secured axially and rotationally inside chamber 245 of barrel 240 at a distal end 241 thereof such that at least a portion of tube 712 extends into tip 243 of syringe 700.

Figure 8A:
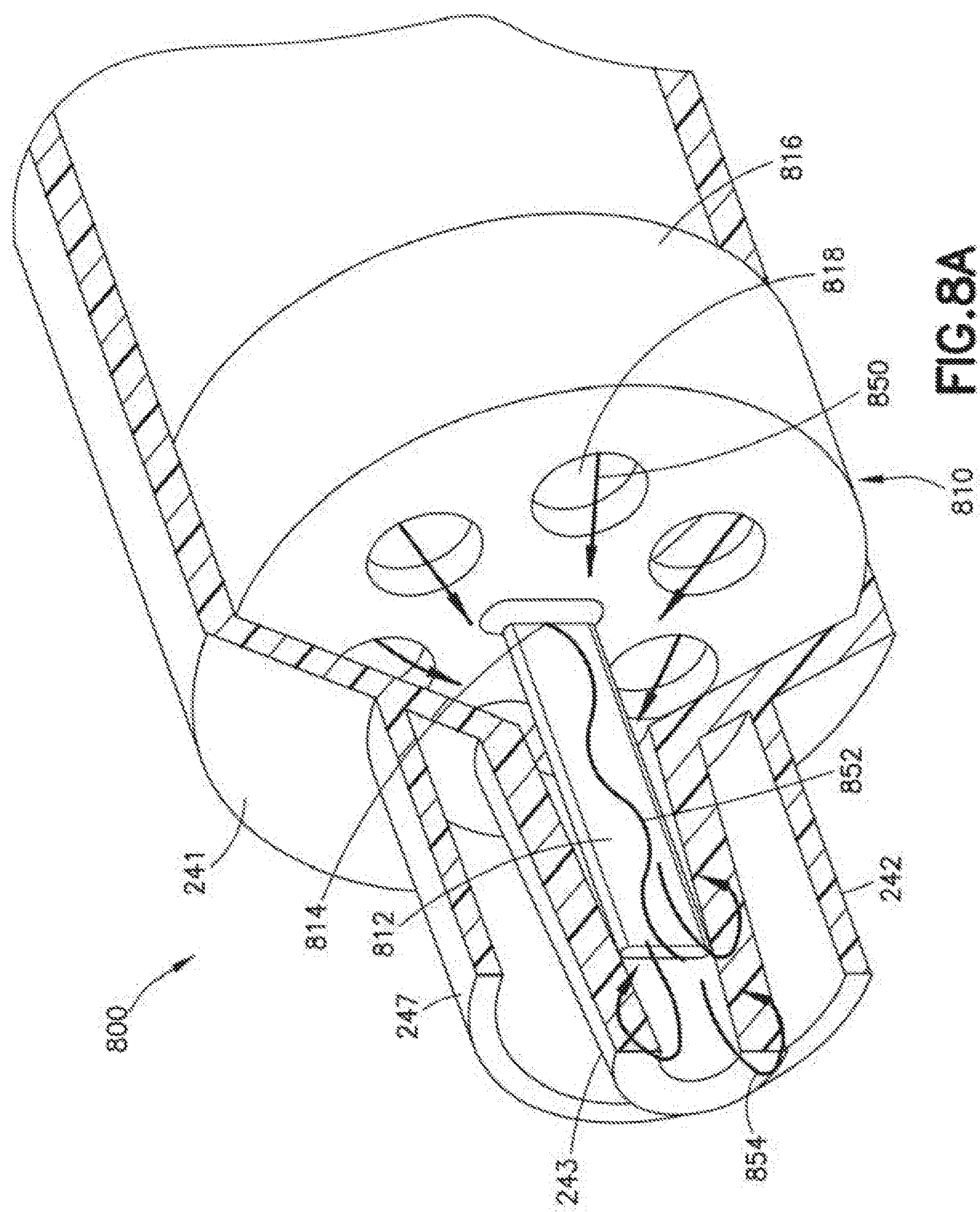
FIGS. 8A, 8B, and 8C illustrate various views of a syringe barrel including a flushing mechanism and various components thereof according to yet another alternative exemplary embodiment of the disclosure.
Figure 8B:
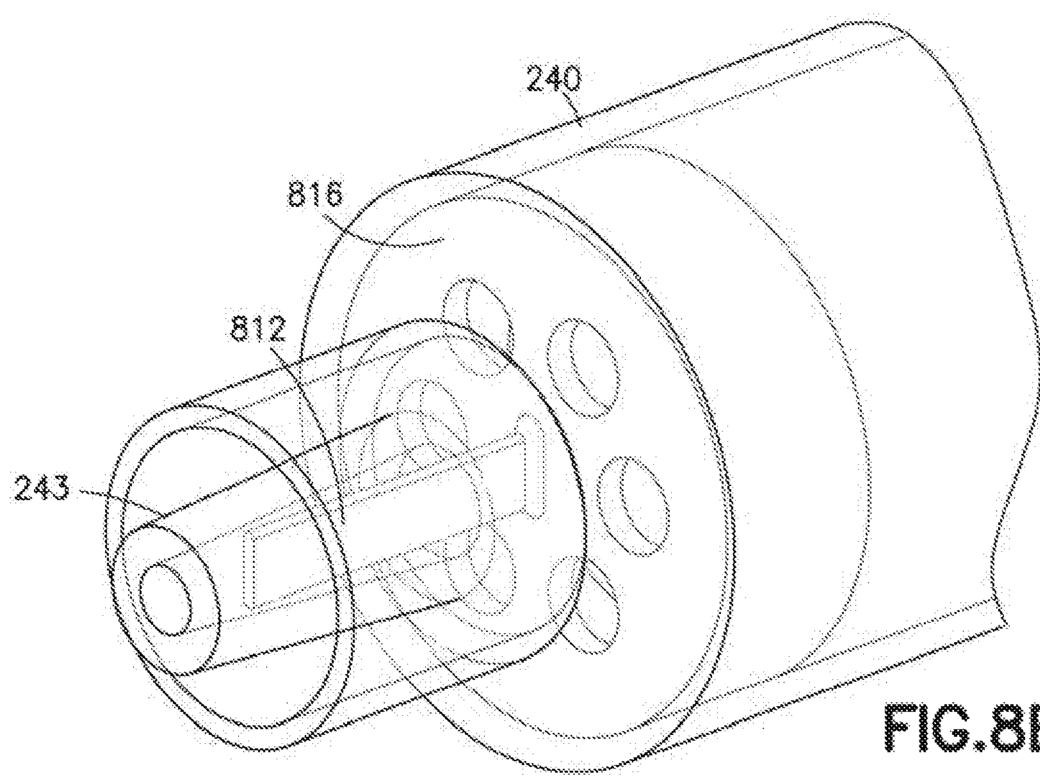
Figure 8C:
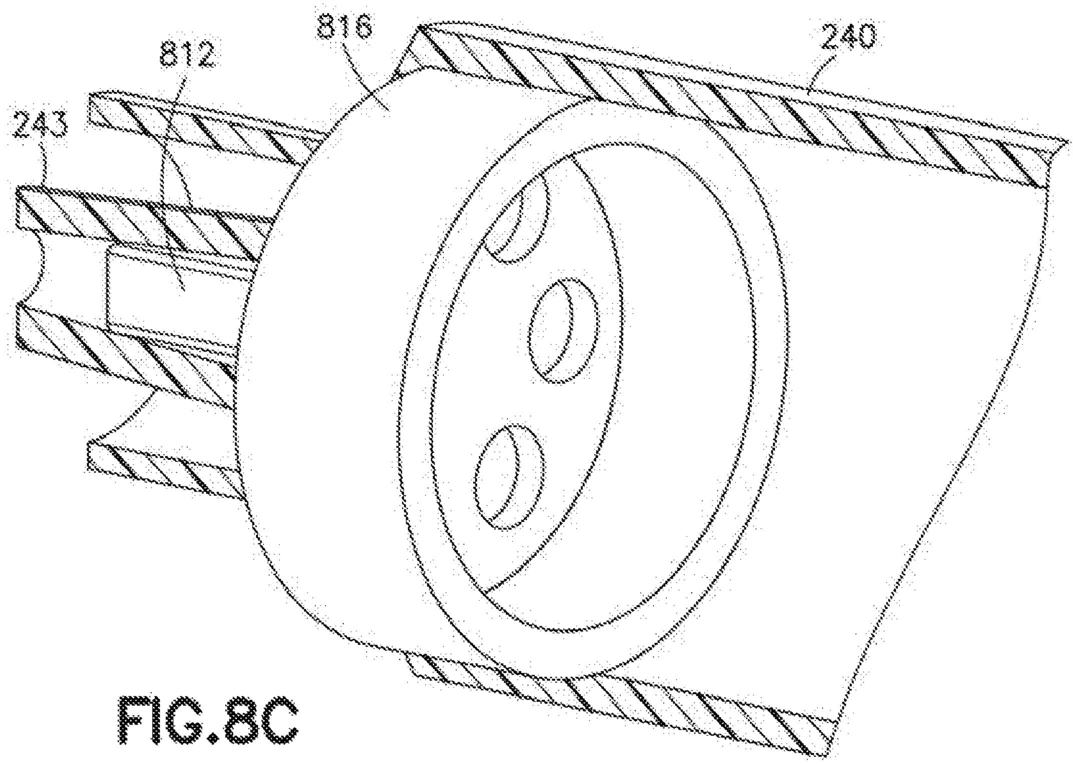

Referring to FIGS. 8A-8C, yet another exemplary alternative implementation of embodiments of the present disclosure provides a syringe 800 having at a distal end 241 of syringe barrel 240 a resonant flushing component 810 comprising a relatively thin, wide, "ribbon-like" member 812 disposed on a ribbon support structure 816 at retaining section 814. Fluid being expelled from barrel 240 of the flush syringe 800 by a moving plunger (not shown) flows 850 through openings 818 in support structure 816 and flows

852 over ribbon 812. In an exemplary implementation, fluid does not flow through the resonant member but rather flow around it. In a non-limiting example of an operation, fluid flowing 852 over the surfaces of the ribbon-like member 812 causes ribbon 812 to flap or flutters due to fluid-structure interaction between vortex shedding and shape of waving ribbon 812, periodically disrupting flow through syringe tip and causing pulsatile flow 842. For example, flapping or fluttering of ribbon 812 alternatingly closes off fluid flow on one side or the other of the ribbon 812 as it alternatingly touches opposing interior walls of syringe tip 243 (or other walls of the syringe body, for example in distal portion 241 of chamber 245). In a non-limiting example, component 810 can be produced as a unitary component and secured axially and rotationally, for example by friction fitting, inside chamber 245 of barrel 240 at a distal end 241 thereof such that at least a portion of ribbon 812 extends into tip 243 of syringe 800.

While the present disclosure has been shown and described with reference to certain exemplary embodiments thereof, it will be understood by those skilled in the art that various changes in form and details may be made therein without departing from the spirit and scope of the embodiments of the present disclosure. Furthermore, any of the features or elements of any exemplary implementations of the embodiments of the present disclosure as describes above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure.

Other objects, advantages and salient features of the disclosure will become apparent to those skilled in the art from the details provided, which, taken in conjunction with the annexed drawing figures, disclose exemplary embodiments of the disclosure.

I claim:

1. A flushing syringe comprising:

a barrel having a sidewall extending from a proximal end to a distal end and defining a chamber accommodating a fluid;

a syringe tip disposed at the distal end of the barrel, the fluid exiting the barrel through the syringe tip; and a wheel configured in the chamber to rotate due to a rotational velocity component in a flow of the fluid from the chamber, and periodically block and unblock the flow of the fluid from the chamber out of the syringe tip, producing a pulsatile flow in the flow of the fluid from the chamber out of the syringe tip, wherein the wheel comprises inclined vanes inducing the rotational velocity component in the flow of the fluid.

2. The flushing syringe of claim 1 wherein the wheel is configured proximate to a distal end of the chamber.

3. The flushing syringe of claim 1, further comprising an orifice plate disposed downstream of the wheel.

4. The flushing syringe of claim 3, wherein the orifice plate is secured axially and rotationally within the barrel.

5. The flushing syringe of claim 3, wherein the wheel is accommodated on the orifice plate.

6. The flushing syringe of claim 5, wherein the orifice plate comprises a first platen with a pin extending from the first platen, and the wheel is rotatably accommodated on the pin.

7. The flushing syringe of claim 6, wherein the orifice plate comprises a groove in an outer perimeter of the first platen for accommodating an O-ring, to facilitate a friction fit of the orifice plate with respect to an interior surface of the sidewall of the barrel.

8. The flushing syringe of claim 6, wherein the wheel comprises a hub having an essentially cylindrical opening to accommodate the pin extending from the first platen allowing a rotational movement of the wheel with respect to the orifice plate.

9. The flushing syringe of claim 8, wherein an axial movement of the wheel with respect to the orifice plate is restricted.

10. The flushing syringe of claim 3, wherein the orifice plate comprises a first opening allowing the flow of the fluid through the orifice plate.

11. The flushing syringe of claim 3, wherein the orifice plate comprises a plurality of first openings, each of said first openings allowing the flow of the fluid through the orifice plate.

12. The flushing syringe of claim 3, wherein the orifice plate is secured axially or rotationally within the barrel.

13. The flushing syringe of claim 3, wherein the orifice plate is friction fitted within the barrel.

14. The flushing syringe of claim 3, wherein the orifice plate is removably fitted within the chamber.

15. The flushing syringe of claim 3, wherein the orifice plate is configured proximate to a distal end of the chamber.

16. The flushing syringe of claim 1, wherein the wheel comprises a second platen having the inclined vanes at a non-ninety degree angle with respect to the second platen.

17. The flushing syringe of claim 16, wherein the second platen comprises at least one second opening allowing the flow of the fluid through the second platen.

* * * * *